(12) United States Patent
Yu et al.

(10) Patent No.: US 11,119,061 B2
(45) Date of Patent: Sep. 14, 2021

(54) BIOPHARMACEUTICAL AGGREGATION ASSESSMENT AND COUNTERFEIT DETECTION USING MAGNETIC RESONANCE RELAXOMETRY

(71) Applicant: UNIVERSITY OF MARYLAND, BALTIMORE, Baltimore, MD (US)

(72) Inventors: Yihua Bruce Yu, Ellicott City, MD (US); Marc Taraban, Gaithersburg, MD (US); Yue Feng, Niantic, CT (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/939,424

(22) Filed: Jul. 27, 2020

(65) Prior Publication Data

US 2021/0010961 A1 Jan. 14, 2021

Related U.S. Application Data

(60) Continuation of application No. 16/682,157, filed on Nov. 13, 2019, now Pat. No. 10,724,974, which is a division of application No. 16/369,534, filed on Mar. 29, 2019, now Pat. No. 10,514,347, which is a division of application No. 14/780,711, filed as application No. PCT/US2014/033833 on Apr. 11, 2014, now Pat. No. 10,267,754.

(Continued)

(51) Int. Cl.
*G01N 24/08* (2006.01)
*G01R 33/44* (2006.01)
*G01N 33/15* (2006.01)
*G01R 33/50* (2006.01)

(52) U.S. Cl.
CPC ............. *G01N 24/08* (2013.01); *G01N 33/15* (2013.01); *G01R 33/448* (2013.01); *G01R 33/50* (2013.01)

(58) Field of Classification Search
CPC ........ G01N 24/08; G01N 33/15; G01R 33/50; G01R 33/448
See application file for complete search history.

(56) References Cited

U.S. PATENT DOCUMENTS 10,267,754 B2 4/2019 Yu et al.
10,514,347 B2 12/2019 Yu et al.
(Continued)

OTHER PUBLICATIONS

Bouchoux, Antoine et al. "Molecular Mobility in Dense Protein Systems: An Investigation through 1 H NMR Relaxometry and Diffusometry." Journal of Physical Chemistry Part B: Condensed Matter, Materials, Surfaces, Interfaces & Biophysical, 2012 (116) (38), 11744-11753.

(Continued)

*Primary Examiner* — G.M. A Hyder
(74) *Attorney, Agent, or Firm* — Tristan A. Fuierer; Olive Law Group, PLLC

(57) ABSTRACT

The present invention generally relates to a method of using NMR relaxation rates ($R_2$) of water molecules as an indicator of the extent of aggregation of biopharmaceutical formulations. The biopharmaceutical can be evaluated non-destructively without the vial or container being opened or protective seal compromised (i.e., broken). The method is applicable to all biopharmaceuticals and the water signal obtained by magnetic resonance relaxometry is very strong and sensitive because water is used as the solvent and is present in high (>90%) concentrations in every biopharmaceutical formulation.

9 Claims, 8 Drawing Sheets

Related U.S. Application Data

(60) Provisional application No. 61/811,401, filed on Apr. 12, 2013.

(56) References Cited

U.S. PATENT DOCUMENTS

| | | | |
|---|---|---|---|
| 10,724,974 | B2 | 7/2020 | Yu et al. |
| 2004/0090231 | A1 | 5/2004 | Augustine et al. |
| 2005/0287527 | A1 | 12/2005 | Ni et al. |
| 2006/0269965 | A1 | 11/2006 | Josephson |
| 2007/0116602 | A1 | 5/2007 | Lee |
| 2010/0072994 | A1 | 3/2010 | Lee et al. |
| 2010/0278829 | A1 | 11/2010 | Edwards, III et al. |
| 2011/0124744 | A1 | 5/2011 | Lee et al. |
| 2012/0100546 | A1 | 4/2012 | Lowery, Jr. |
| 2012/0164644 | A1 | 6/2012 | Neely et al. |
| 2013/0244238 | A1 | 9/2013 | Neely et al. |
| 2013/0265054 | A1 | 10/2013 | Lowery, Jr. |

OTHER PUBLICATIONS

Daskiewicz, O. et al. "Proton Magnetic Relaxation and Protein Hydration." Nature, 1963 (200) (4910), 1006-1007.

Mahler, Hans-Christian et al. "Protein aggregation: Pathways, induction factors and analysis." Journal of Pharmaceutical Sciences, 2009 (98) (9), 2909-2925.

Baroni, et al. "Relaxometric Characterization of Balsamic Vinegar." meeting abstract 6th Conference on Field Cycling NMR Relaxometry Turin (Italy) Jun. 4, 2009.

Bloembergen, N. et al. "Relaxation Effects in Nuclear Magnetic Resonance Absorption." Phys. Rev. 1948, 73, 679-712.

Dalvit, C. et al. "High-Throughput NMR-Based Screening with Competition Binding Experiments." J. Am. Chem. Soc. 2002, 124, 7702-7709.

Fanali, G. et al. "Human serum albumin: From bench to bedside." Mol. Asp. Med. 2012, 33, 209-290.

Korzhnev, D. et al. "Probing Invisible, Low-Populated States of Protein Molecules by Relaxation Dispersion NMR Spectroscopy: An Application to Protein Folding." Acc. Chem. Res., 2008, 41, 442-451.

Krayukhina, E. et al. "Aggregation analysis of pharmaceutical human immunoglobulin preparations using size-exclusion chromatography and analytical ultracentrifugation sedimentation velocity." J. Biosci. Bioeng. 2012, 115, 104-110.

Mao, X. et al. "Understanding Radiation Damping in a Simple Way." Concepts Magn. Reson. 1997, 9, 173.

Metz, H. et al. "Benchtop-NMR and MRI—A new analytical tool in drug delivery research." Int. J. Pharm. 2008, 364, 170-175.

Oliva, A. et al. "Influence of temperature and shaking on stability of insulin preparations: degradation kinetics." Int. J. Pharm. 1996, 143, 163-170.

Saso, L. et al. "Effect of Selected Substances on Heat-Induced Aggregation of Albumin, IgG and Lysozyme." Res. Commun. Pathol. Pharmacol. 1998, 102, 15-28.

BIOPHARMACEUTICAL AGGREGATION ASSESSMENT AND COUNTERFEIT DETECTION USING MAGNETIC RESONANCE RELAXOMETRY

CROSS REFERENCE TO RELATED APPLICATIONS

This application is a continuation of, and claims priority to, U.S. patent application Ser. No. 16/682,157 filed on Nov. 13, 2019, now U.S. Pat. No. 10,724,974, which is a divisional of U.S. patent application Ser. No. 16/369,534 filed on Mar. 29, 2019, now U.S. Pat. No. 10,514,347, which is a divisional of U.S. patent application Ser. No. 14/780,711 filed on Sep. 28, 2015, now U.S. Pat. No. 10,267,754, which was filed under the provisions of 35 U.S.C. § 371 and claims priority of International Patent Application No. PCT/US2014/033833 filed on Apr. 11, 2014, which in turn claims priority to U.S. Provisional Patent Application No. 61/811,401 filed Apr. 12, 2013 in the name of Yihua Bruce Yu entitled "Assessing Biopharmaceutical Aggregation Using Magnetic Resonance Relaxometry," all of which are incorporated by reference herein in their entirety.

STATEMENT OF FEDERALLY SPONSORED RESEARCH

This invention was made with government support under Grant Number U01FD004320 awarded by the U.S. Food and Drug Administration and Grant Number CBET1133908 awarded by the National Science Foundation. The government has certain rights in the invention.

FIELD

The present invention relates to methods for assessing the extent of biopharmaceutical aggregation and to methods of detecting counterfeit biopharmaceuticals using magnetic resonance relaxometry.

DESCRIPTION OF THE RELATED ART

Aggregation is a significant problem in biopharmaceutical manufacturing and storage. Aggregated proteins have lower or no biological activity, are more likely to elicit an immune response, may have an altered biodistribution, and may have altered pharmacokinetics. Disadvantageously, most protein or peptide aggregation is not visible to the naked eye and can only be detected by scientific instruments.

Problems of quality control of pharmaceutical products in aqueous solutions become more and more pressing with the fast growing number of drugs based on biomacromolecules (e.g., proteins, nucleic acids, polysaccharides, etc.). One of the earliest signs of degradation of aqueous pharmaceutical preparations is the aggregation of the active factor during the manufacturing or long-term storage of the product [1]. Even in the past, when the number of protein-based biotherapeutics was quite limited (e.g., to insulin, γ-globulin, albumin, etc.), the monitoring of aggregation was a time-consuming and complex process [2]. In the modern pharmaceutical industry, the main techniques to detect such soluble aggregates include size-exclusion chromatography (SEC), analytical ultracentrifugation sedimentation velocity (AUC-SV), dynamic light scattering (DLS), electrophoresis, and field-flow fractionation [2]. Disadvantageously, all of these conventional techniques could be regarded as "destructive," since their application by definition requires the opening of the vial and renders the drug unusable even if it is not considered degraded. Moreover, these conventionally used techniques are time-consuming, which precludes their efficient application for high-throughput quality checks post-production.

Recent breakthrough developments in the instrumentation for nuclear magnetic resonance (NMR) spectroscopy and imaging have opened up opportunities to design novel nondestructive analytical techniques for the pharmaceutical industry. Using NMR relaxation measurements, high-throughput NMR screening has been actively used to identify molecules with a high affinity to a receptor at very low concentrations [3]. The analytical procedures become significantly faster with the application of commercially available computer-controlled NMR autosamplers. Of special importance was the appearance of commercially available, relatively inexpensive benchtop NMR and magnetic resonance imaging (MM) instruments and relaxometers [4]. These instruments, working at the magnetic field strength of 0.3-0.5 T have already demonstrated their extreme versatility in the chemical and food industry, and very recently, in the monitoring of drug delivery steps in vitro, for example, the hydration and swelling of controlled release tablets [4]. Benchtop NMR relaxometers enable highly accurate measurements of nuclear spin relaxation times $T_1$ and $T_2$. Moreover, most of these instruments have a permanent or electronically cooled magnet with the variable bore from 10 mm to 25 mm which provides a great flexibility in the measurements of vials of various sizes.

Clearly, there is a need for a fast and reliable technique which would allow one to nondestructively measure the extent of degradation of the pharmaceutical preparation and still retain its usability. Towards that end, the present invention relates to a method of using NMR relaxation rates ($R_1$ and $R_2$) of water molecules as an indicator of the aggregation of biopharmaceutical formulations. Advantageously, the method described herein is not drug specific, is easy to use, is nondestructive, and fast. Further, the NMR relaxation rates ($R_1$ and $R_2$) of water can be used to detect counterfeit biopharmaceutical-containing compositions by using the magnetic resonance relaxometry of water to obtain field strength dependency of the relaxation rate (relaxation dispersion profile) to detect the deviations in the content of ingredients in the complex mixtures of biopharmaceuticals in order to identify whether the biopharmaceuticals are counterfeited.

SUMMARY

The present invention generally relates to a method of using NMR relaxation rates ($R_1$ and $R_2$) of water molecules as an indicator of the aggregation of biopharmaceutical formulations. The biopharmaceutical can be evaluated without the vial or container being opened or protective seal compromised (i.e., broken). The method is applicable to all biopharmaceuticals and the signal obtained by magnetic resonance relaxometry is very strong and sensitive because water is used as the solvent in high (>90%) concentrations in every biopharmaceutical formulation.

The present invention also relates to a method of using NMR relaxation rates ($R_1$ and $R_2$) dispersion profile of water molecules to detect counterfeit compositions, for example, counterfeit biopharmaceutical-containing compositions.

In one aspect, a method of measuring the extent of aggregation of a biopharmaceutical in a biopharmaceutical-containing product is described, said method comprising measuring the transverse relaxation rate of water $R_2$ in the biopharmaceutical-containing product, and extrapolating the extent of aggregation of the biopharmaceutical from a standard calibration curve using the measured $R_2$ of water.

In another aspect, a method of detecting counterfeit compositions comprises: measuring a relaxation dispersion profile $R(\omega)$ of the composition, and comparing the measured $R(\omega)$ to a standard $R(\omega)$ for that composition, wherein the composition is a counterfeit if the measured $R(\omega)$ is greater than an indicated percent difference from the standard $R(\omega)$, wherein the indicated percent difference is provided by the manufacturer of the composition, and wherein the measurement of the relaxation dispersion profile $R(\omega)$ is done non-destructively. The composition can be a biopharmaceutical-containing product.

Other aspects, features and advantages of the invention will be more fully apparent from the ensuing disclosure and appended claims.

DETAILED DESCRIPTION, AND PREFERRED EMBODIMENTS THEREOF

Figure 1A:
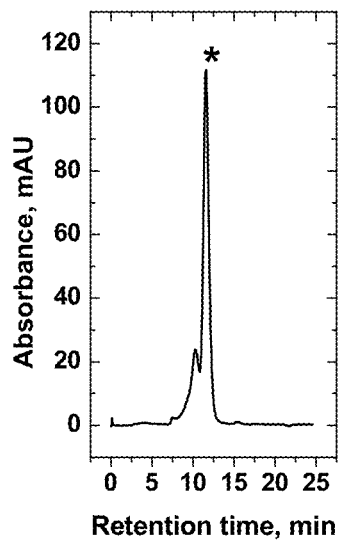
FIG. 1(a) illustrates SEC chromatograms of BSA solution (75 μM) at 25° C. prior to heating.

The present invention generally relates to a method of using NMR relaxation rates (longitudinal and transverse relaxation rate constants, $R_1$ and $R_2$, respectively) of water molecules as an indicator of the extent of aggregation of biopharmaceuticals in biopharmaceutical-containing products. Further, the present invention relates to a method of detecting counterfeit compositions, e.g., biopharmaceutical-containing compositions, using the NMR relaxation rates ($R_1$ and $R_2$) of water.

Advantageously, the method described herein is a reliable and simple method to detect biopharmaceutical aggregation and hence, viability, and has application as a quality control tool for biopharmaceuticals. The method enables the calculation of the extent of aggregation in biopharmaceuticals non-destructively, without opening the vial or storage container, by measuring the nuclear spin relaxation rate constant, $R_1$ and $R_2$, of water as a quality control parameter. The nuclear spin relaxation rate constant can be measured before dispensing the biopharmaceutical to the patient to confirm that the extent of aggregation is within an acceptable range. Accordingly, this method redefines the conventional methods of evaluating shelf-life of biopharmaceuticals by assessing their precise extent of aggregation for each vial or storage container.

As defined herein, the "biopharmaceutical" includes antibodies, proteins, peptides, nucleic acids, polysaccharides, and combinations thereof.

As used herein, "counterfeit" compositions, e.g., biopharmaceuticals, correspond to compositions sold or provided under a specific brand or generic name that are not manufactured by or on behalf of the owner of the brand name or a provider of a generic composition. Often the counterfeit compositions are purchased online at a lower cost and are not made according to the exact manufacturing standards of the owner of the brand name or provider of a generic composition and/or are less efficacious than the brand name or generic composition.

As defined herein, a "vial" corresponds to a small glass (optionally, plastic, ceramic, etc., anything nonmetal) vessel, bottle or ampoule used to store the biopharmaceutical. The vial can have a screw top, a top that is closed using a cork or plastic stopper, a crimp vial (closed with a rubber stopper and a metal cap), a flip-top or snap cap. The vial can be tubular, or have a bottle-like shape with a neck. Other types and shapes of vials used to store biopharmaceuticals as well as capping means are readily understood by the person skilled in the art.

As defined herein, a "non-destructive" measurement is defined as a measurement performed without opening the vial or otherwise accessing the contents of the vial (for example by withdrawing a portion through a rubber gasket). Moreover, a non-destructive measurement means that no additives or probes or the like are added to the vial prior to the measurement of the transverse relaxation rate of water $R_2$ in the biopharmaceutical-containing product.

The present inventors have surprisingly discovered that the relaxation rate ($R_1$ and $R_2$) of water increases depending on the extent of biopharmaceutical aggregation and the size distribution of the aggregates. Because water is present in every biopharmaceutical formulation, this method provides a universally applicable method to assess the degree of biopharmaceutical aggregation using magnetic resonance relaxometry. The NMR/MRI-based nondestructive technique involves the measurement of the NMR relaxation rates of water molecules in biopharmaceutical products. Such measurements can be performed using commercially available, relatively inexpensive benchtop NMR and MRI instruments and relaxometers and are "nondestructive" and "non-disruptive" in that they could be performed without opening the vial and as such, after the analysis, the biopharmaceuticals of acceptable quality could still be used. That said, it should be appreciated that the measurements can occur destructively as well, whereby the vial is opened.

Accordingly, in one aspect, a method of measuring the extent of aggregation of a biopharmaceutical in a biopharmaceutical-containing product, said method comprising measuring the transverse relaxation rate of water $R_2$ in the biopharmaceutical-containing product, and extrapolating the extent of aggregation of the biopharmaceutical from a standard calibration curve using the measured $R_2$ of water. The extent of aggregation can be the percent aggregation of the biopharmaceutical, the concentration of the biopharmaceutical aggregates, or the molecular weight of the biopharmaceutical aggregates.

The transverse relaxation rate of water can be used as a quality control parameter for biopharmaceuticals, wherein the water relaxivity is measured during manufacturing at a specified temperature and the result listed in the package insert of the biopharmaceutical product. Distributors, hospitals and pharmacies can then use benchtop NMR or MRI instruments and relaxometers to measure water relaxivity at a specified temperature and compare it with the value listed in the package insert before distribution or usage. If the extent of aggregation is outside of an acceptable limit, the biopharmaceutical product should not be distributed or used.

Further, the method described herein is fast and reliable and allows the user to nondestructively measure the extent of aggregation, and hence degradation, of the pharmaceutical preparation and still retain its usability if no aggregation is detected. The method is not drug specific and is easy to use.

A non-exclusive list of biopharmaceutical products that can be measured for the extent of aggregation includes, but is not limited to, bovine serum albumin; human serum albumin; human γ-globulin; hormones such as insulin, glucagon, gonadotrophins, and growth hormone; haematopoietic growth factors such as erythropoetin; blood factors such as Factor VIII and Factor IX; thrombolytic agents; interferons such as interferon-α, interferon-β, and interferon-γ; interleukin-based products such as interleukin-2; vaccines such as the influenza vaccine; monoclonal antibodies such as adalimumab, rituximab, infliximab, trastuzumab, ustekinumab, denosumab, and golimumab, and including fragments of monoclonal antibodies (e.g., Fc and Fab fragments), variants of monoclonal antibodies, such as single-chain antibodies, bivalent antibodies, and the like, and polyclonal antibody preparations for research or clinical use including therapeutic antibody preparations such as intravenous immunoglobulin (IVIG); tumor necrosis factor; abatacept; alefacept; etanercept; denileukin diftitox; OPTISON; NEUPOGEN; albumin; and ribonuclease A, to name a few.

In practice, the standard for aggregation in the biopharmaceutical sample should be determined by the manufacturer. The manufacturer can provide the calibration curve (line) of relaxation rate $R_2$ versus the extent of aggregation (e.g., percent aggregation) measured at a given temperature (e.g., 25° C.). It could be either in the form of a formula or the graphic (like nomogram, etc.). The user will then measure the $R_2$ of water of the biopharmaceutical sample at the same temperature and compare the value with the standard calibration curve, as understood by the person skilled in the art. The manufacturer will also provide a maximum acceptable extent of aggregation value or maximum water $R_2$ value for the biopharmaceutical, relative to the extent of aggregation at the time of production, whereby the biopharmaceutical is overly degraded (i.e., no longer viable) and should not be dispensed. It should be appreciated that the standard calibration curve can be prepared by the user, if necessary, and that the maximum acceptable extent of aggregation will vary according to the biopharmaceutical.

It should be appreciated by the person skilled in the art that the methods described herein can be used to measure the extent of aggregation of a biopharmaceutical in a biopharmaceutical-containing product during pre-formulation, formulation, production, or post-production.

In another aspect, a method of determining if a biopharmaceutical in a biopharmaceutical-containing product remains viable is described, said method comprising measuring the transverse relaxation rate of water $R_2$ in the biopharmaceutical-containing product, extrapolating the extent of aggregation of the biopharmaceutical from a standard calibration curve using the measured $R_2$ of water, and comparing the extent of aggregation to the maximum acceptable extent of aggregation for the biopharmaceutical, relative to the extent of aggregation at the time of production, to determine viability of the biopharmaceutical. The extent of aggregation can be the percent aggregation of the biopharmaceutical, the concentration of the biopharmaceutical aggregates, or the molecular weight of the biopharmaceutical aggregates.

In another aspect, a kit for determining the extent of aggregation of a biopharmaceutical in a biopharmaceutical-containing product is described, said kit comprising instructions on measuring the transverse relaxation rate of water $R_2$ in a biopharmaceutical-containing product, a standard calibration curve for the biopharmaceutical, and a maximum acceptable extent of aggregation, wherein the maximum acceptable extent of aggregation for the biopharmaceutical is determined relative to the extent of aggregation of the biopharmaceutical at the time of production.

In yet another aspect, a method of preparing the standard calibration curve for a biopharmaceutical is described, said method comprising:

selecting a temperature whereby the biopharmaceutical will experience a higher rate of aggregation;

exposing the biopharmaceutical to the temperature for at least two, three, four, or five time periods;

measuring the transverse relaxation rate of water $R_2$ in the biopharmaceutical at the at least two, three, four, or five time periods;

measuring the percent aggregation of the biopharmaceutical using size exclusion chromatography at the at least two, three, four, or five time periods; and plotting the percent aggregation relative to the transverse relaxation rate of water $R_2$ and determining the best-fit regression line.

With regards to this aspect of the invention, for the purposes of standard calibration curve, the concentration of the aggregates and/or the percentage of aggregation are measured by means of size-exclusion chromatography, it would be appreciated by those skilled in the art that other methods could be also employed including, but not limited to, ultracentrifugation, dynamic light scattering, small-angle X-ray and/or neutron scattering. Also, the person skilled in the art will easily recognize other techniques to induce aggregation of the biopharmaceuticals in addition to heat-induced aggregation, such as light-induced, ultrasound-induced, and shaking, to name a few. All above techniques are incorporated herein in their entirety by reference.

In still another aspect, the NMR relaxation rates ($R_1$ and $R_2$) of water could be used to detect counterfeit compounds, e.g., biopharmaceuticals and/or counterfeit complex mixtures of said bioparmaceuticals, in a composition, e.g., a biopharmaceutical-containing product. It is well-known to the person skilled in the art that NMR relaxation rates ($R_1$ and $R_2$) are field-dependent, i.e., they both depend on magnetic field strength and hence, the resonance frequency ω [5]. Such dependency, in the form of R(ω) is called a relaxation dispersion profile. The technique to measure R(ω) is called magnetic resonance relaxometry (MRR). The inventors surprisingly discovered that the transverse relaxation rate constant of water $R_2$ is very sensitive toward a variety of conditions of a complex mixture, in particular, the composition of a mixture of biopharmaceuticals, drugs, cosmetics, etc. In this aspect, the MRR of water signal will be used to detect the deviations in the content of ingredients in the complex mixtures in order to identify whether the mixtures are counterfeited. In practice, the unique composition will be characterized by the unique relaxation dispersion profile R(ω), a "magnetic fingerprint" measured by MRR and provided by the manufacturer of the proprietary composition, optionally, placed on the manufacturer's website. The user then could measure the relaxation dispersion profile R(ω) of a composition purchased on the market under the manufacturer's brand name and after comparing it with the "magnetic fingerprint" of said composition would be able to identify potentially counterfeited compositions. Such measurements are nondestructive in that they could be performed without opening the vial and accordingly, after the analysis the compositions which are not counterfeited could still be used. Measurements of the relaxation dispersion profile R(ω) could be performed using relatively inexpensive benchtop relaxometers for MRR experiments, such as, for example, SMARtracer FFC relaxometer operated in the range from 2.5 mT to 250 mT (STELAR s.r.l, Mede, Italy). Accordingly, the method of detecting counterfeit compositions comprises: measuring a relaxation dispersion profile R(ω) of the composition, and comparing the measured R(ω) to a standard R(ω) for that composition, wherein the composition is a counterfeit if the measured R(ω) is greater than an indicated percent difference from the standard R(ω), wherein the indicated percent difference is provided by the manufacturer of the composition, and wherein the measurement of the relaxation dispersion profile R(ω) is done non-destructively. For example, the method can be used for detecting counterfeit biopharmaceutical-containing products, wherein said method comprises: measuring a relaxation dispersion profile R(ω) of the biopharmaceutical-containing product, and comparing the measured R(ω) to a standard R(ω) for that biopharmaceutical-containing product, wherein the biopharmaceutical-containing product is a counterfeit if the measured R(ω) is greater than an indicated percent different from the standard R(ω), wherein the indicated percent difference is provided by the manufacturer, and wherein the measurement of the relaxation dispersion profile R(ω) is done non-destructively. It should be understood by the person skilled in the art that the indicated percent difference calculated as an average deviation between the measured and standard R(ω) dispersion profile may be a percentage such as 0.1%, 0.5%, 1%, 2%, 3%, 4%, or 5%, depending on the composition, e.g., biopharmaceutical-containing product, and known variations that may occur during storage and transportation.

The features and advantages of the invention are more fully shown by the illustrative examples discussed below.

EXAMPLE 1

Solutions of bovine serum albumin (BSA) in phosphate buffered saline (PBS) were used as a model system for protein-based pharmaceuticals. BSA is readily commercially available and is also widely used in many medical applications [6]. The NMR relaxivities of water ($R_1$ and $R_2$) were measured in freshly prepared protein solutions and in the solutions with a controlled degree of protein aggregation. To mimic protein aggregation in biopharmaceutical products, a heat-induced aggregation method was used [7]. The slow aggregation process in model systems that occurs during prolonged standing at room temperature was also evaluated.

Analytical grade reagents for buffer preparation, solvents and bovine serum albumin (BSA, lyophilized, 98% purity, molecular weight 66 kDa) were purchased from Sigma Aldrich Inc., St. Louis, Mo., and were used without further purification. All solutions were prepared in phosphate buffered saline (PBS) containing 50 mM sodium phosphate and 100 mM sodium chloride in ultrapure $H_2O$ (resistance 18 MOhm) at pH 7.4.

Heat-induced aggregation of BSA in aqueous solution was monitored using SEC. To study the formation of BSA aggregates at different time points of exposure to heat, the solutions of BSA in PBS buffer at eight different concentrations (30 μM, 75 μM, 110 μM, 150 μM, 230 μM, 310 μM, 380 μM, 455 μM) were heated in water baths at 60° C. for 15 min and 30 min, respectively. After cooling down to 25° C., the concentration of the BSA aggregates was measured by size-exclusion chromatography using the Äkta FPLC system (Amersham Pharmacia Biotech, Inc., Uppsala, Sweden) with UPC-900 UV-detector set at 280 nm. Column: Superose 12 100/300 GL (GE Healthcare, Little Chalfont, UK), 24 mL bed volume, particle size 1 μm, 3 kDa molecular weight cutoff. Injection sample volume: 200 μL. Eluent: PBS buffer at pH 7.4 with 1% sodium azide. Flow rate: 0.5 mL/min. Concentrations of the initial pure (non-aggregated) BSA and its aggregates after the exposure to heat were estimated from the chromatographic peaks areas using the subroutine *Peak Fit Analysis* in Origin 8.1 (OriginLab Co., Northhampton, Mass.). Quality of the nonlinear peak fit was always $R^2$=0.97-0.99.

Figure 1B:
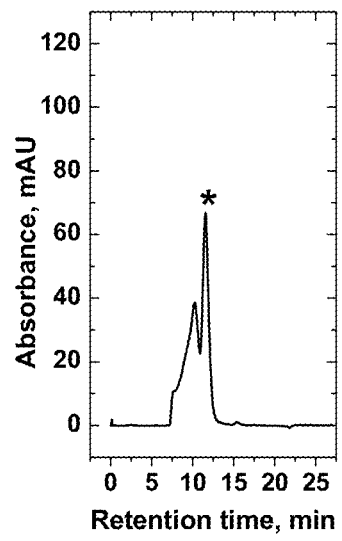
FIG. 1(b) illustrates SEC chromatograms of BSA solution (75 μM) at 25° C. after 15 min at 60° C.
Figure 1C:
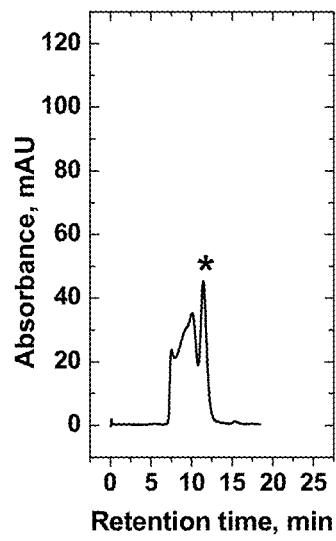
FIG. 1(c) illustrates SEC chromatograms of BSA solution (75 μM) at 25° C. after 30 min at 60° C.
Figure 1D:
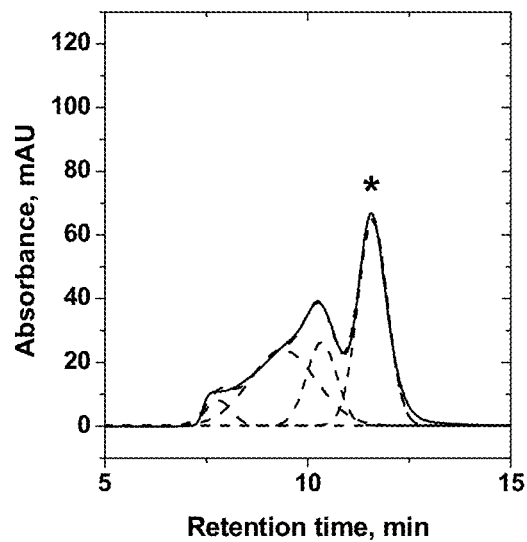
FIG. 1(d) illustrates the peak fit analysis of the expanded SEC chromatogram from FIG. 1(b) using Origin 8.1.

FIG. 1 illustrates the SEC chromatograms of BSA at 30 μM before and after heating, wherein FIG. 1(a) shows the aggregation at 25° C. prior to heating, FIG. 1(b) shows the aggregation after 15 min at 60° C., and FIG. 1(c) shows the aggregation after 30 min at 60° C. It can be seen that the peaks that correspond to larger aggregates grow at the expense of the peak to non-aggregated BSA (designated by the asterisk). Deconvolution of the SEC chromatogram of FIG. 1(b) makes it possible to analyze the extent of aggregation. To calculate the concentration of the BSA aggregates, formula (1) is used:

$$[C]_{agg} = \frac{S_{tot} - S_{BSA}}{S_{tot}}[C]_{BSA} \quad (1)$$

where $S_{tot}$ is the sum of the areas of all peaks resulting from the multiple peak analysis (see, solid line in FIG. 3(d)), $S_{BSA}$ is the area of the peak from non-aggregated BSA (the peak labeled with the asterisk), $[C]_{BSA}$ is the initial concentration of BSA prior to heating, and $[C]_{agg}$ is the concentration of BSA aggregates. The goodness of fitting parameter is $R^2$=0.99. The concentrations of the BSA aggregates, as determined using formula (1) after 15 min and 30 min at 60° C., are tabulated in Table 1.

TABLE 1

Concentrations of the BSA aggregates after 15 min and 30 min of the heat-induced aggregation at 60° C.

| Initial BSA concentration, µM | BSA aggregates after 15 min at 60° C., µM | BSA aggregates after 30 min at 60° C., µM |
|---|---|---|
| 30 | 13 | 15 |
| 75 | 39 | 45 |
| 106 | 65 | 69 |
| 151 | 95 | 98 |
| 227 | 150 | 162 |
| 303 | 176 | 184 |
| 379 | 234 | 242 |
| 455 | 255 | 263 |

Figure 2:
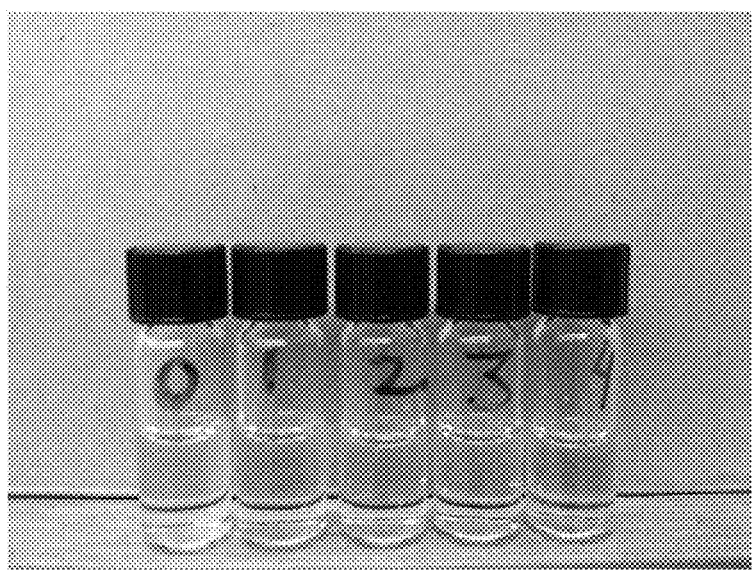
FIG. 2 illustrates the inability to visibly see aggregates formed upon heating with the naked eye.

In order to study the effect of protein aggregation on the longitudinal $R_1$ and transverse $R_2$ relaxation rate constants of water, diluted ($10^{-5}$-$10^{-4}$ M) solutions of bovine serum albumin (BSA) were used as a model system for protein-based preparations. Albumins are known to form aggregates under short (minutes) exposure to moderate temperatures (50-70° C.) [8]. The aggregates formed upon heating are not visible to the naked eyes (see, FIG. 2, wherein vial 0 is PBS; vial 1 is 450 µM BSA in PBS, never heated; vial 2 is 230 µM BSA in PBS, heated for 30 min at 60° C.; vial 3 is 150 µM BSA in PBS, heated for 30 min at 60° C.; and vial 4 is 75 µM BSA in PBS, heated for 30 min at 60° C.).

To study how the relaxation rate constants of water, $R_1$ and $R_2$, correlate with the extent of protein aggregation, BSA solutions of eight different concentrations (30 µM, 75 µM, 110 µM, 150 µM, 230 µM, 310 µM, 380 µM, 450 µM, same as in SEC measurements) were prepared. Each solution was divided into three portions: one portion stayed at 25° C.; one portion was heated to 60° C. for 15 min and then cooled back to 25° C. for measurement; one portion was heated to 60° C. for 30 min and then cooled back to 25° C. for measurement. All NMR experiments were carried on a 400 MHz (9.4 T) Varian NMR spectrometer.

Because water is the solvent, its NMR signal is very strong. To avoid the radiation damping effect in relaxation measurements of water, saturation-recovery and CPMG sequence with a small flip-angle excitation pulse were applied [8]. The flip-angle of the excitation pulse (small-angle) varies depending on the strength of the water signal.

Figure 3A:
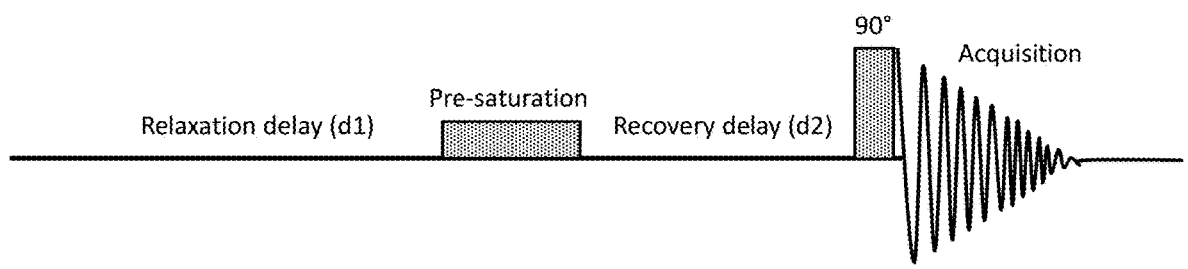
FIG. 3(a) illustrates the pulse sequence for a saturation-recovery experiment.

To measure the longitudinal relaxation rate constant $R_1$, saturation-recovery experiments were used. Referring to FIG. 3(a), the relaxation delay (d1) was 15 s. A 2 second pre-saturation pulse was applied to saturate the water signal before the recovery time. Ten different $T_1$ recovery times (d2=0.1, 0.2, 0.35, 0.6, 1, 1.8, 3, 5, 8 and 12 s) were applied to get a fully recovered water signal. The longitudinal relaxation time $T_1$ (=$1/R_1$) can be extracted by fitting the experimental data to Formula (2):

$$I(t)=I_0\times[1-\exp(-t/T_1)] \quad (2)$$

where I(t) is the $^1H_2O$ signal intensity at time t, $I_0$ is the $^1H_2O$ signal intensity when the signal is fully recovered, and t is the $T_1$ recovery time.

Figure 3B:
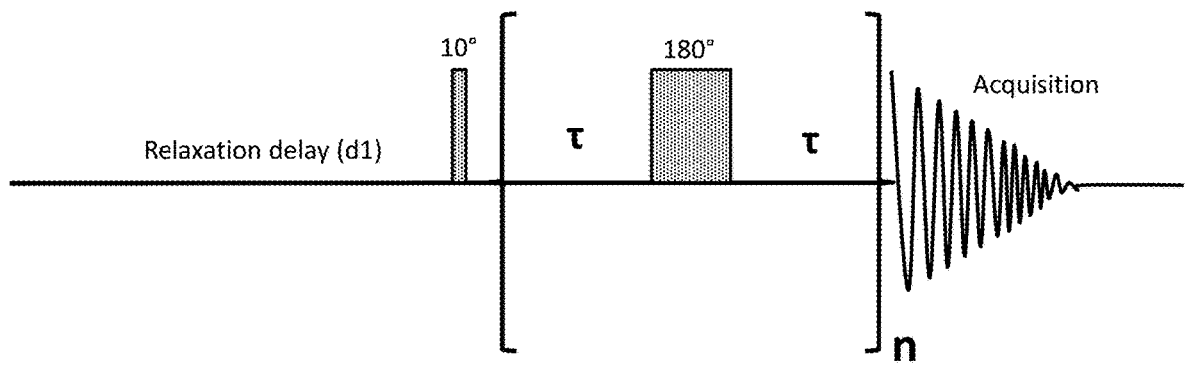
FIG. 3(b) illustrates the pulse sequence for a CPMG experiment. The flip-angle of the excitation pulse (small-angle) varies depending on the strength of the water signal.

To measure the transverse relaxation rate constant $R_2$, Carr-Purcell-Meiboom-Gill (CPMG) experiments were used. Referring to FIG. 3(b), the relaxation delay (d1) is 15 s, the interval between 180° pulses is 120 µs (2τ=120 µs). A small-angle excitation pulse (flip angle about)10° was used to prevent the strong water signal from overflowing the receiver. The said flip-angle of the excitation pulse (small-angle) varies depending on the strength of the water signal. Ten different $T_2$ delay times (2nτ, n is the number of 180°-pulses) was used to get sufficient signal decay (about 90%). The CPMG delay '2nτ' was optimized based on the $T_2$ value of each sample (to get a properly distribution of 10 data point in the whole signal decay curve). For example, for the sample with a BSA concentration of 455 µM, the 10 CPMG delay times were set to: 0.1, 0.25, 0.4, 0.6, 0.8, 1.0, 1.3, 1.6 ,2.0 ,2.4 s. For the sample with a BSA concentration of 30 µM, the 10 CPMG delays were set to: 0.1, 0.3, 0.5, 0.8, 1.1, 1.5, 1.9, 2.5, 3.0, 3.7, 4.5 and 5.5 second. The transverse relaxation time $T_2$ (=$1/R_2$) value can be extracted by fitting experimental data to Formula (3):

$$I(t)=I_0\times\exp(-t/T_2) \quad (3)$$

where I(t) is the $^1H_2O$ signal intensity at time t, $I_0$ is the initial $^1H_2O$ signal intensity when t=0, and t is the $T_2$ delay time.

Figure 4A:
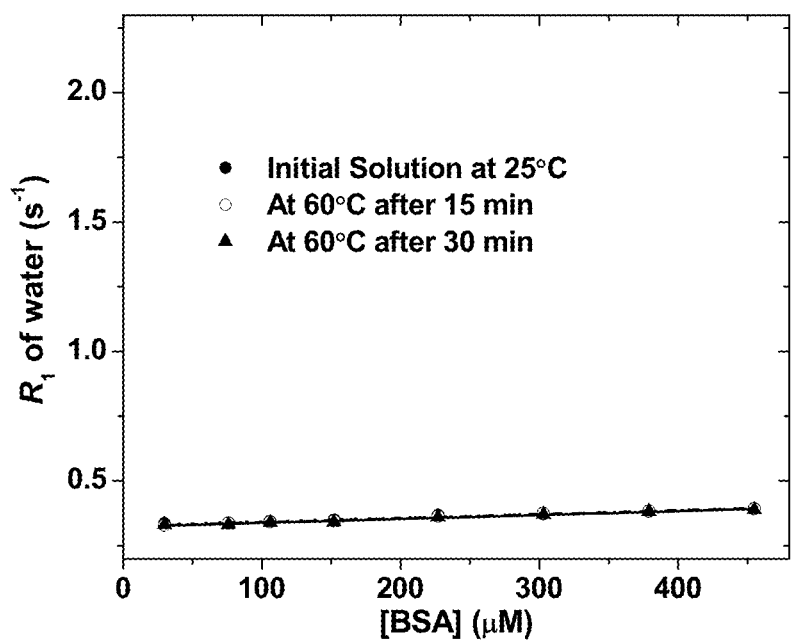
FIG. 4(a) illustrates the dependence of the longitudinal relaxation rate of water $R_1$ on the concentration of BSA, and the buildup of the aggregates after the solutions with different initial concentrations were exposed to heat (60° C.).
Figure 4B:
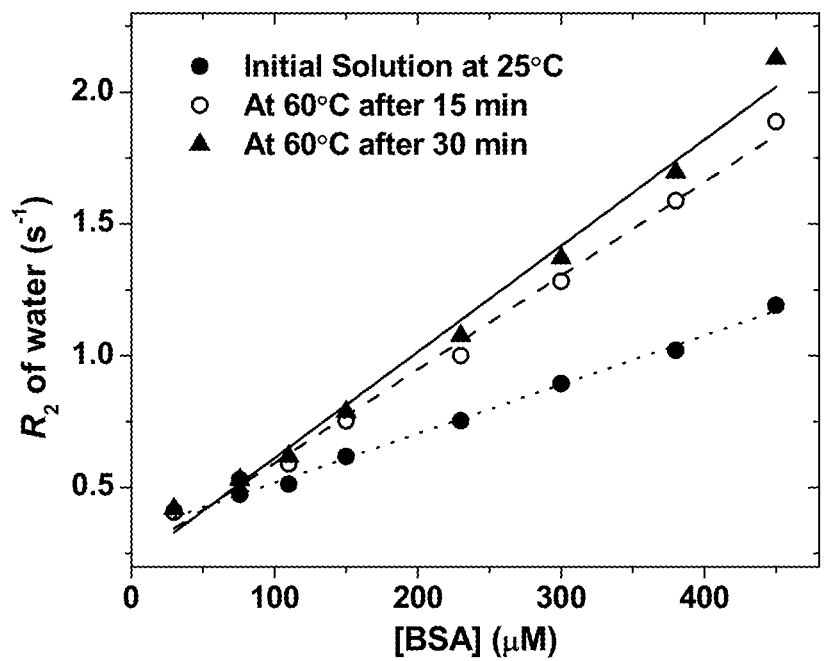
FIG. 4(b) illustrates the dependence of the transverse relaxation rate of water $R_2$ on the concentration of BSA, and the buildup of the aggregates after the solutions with different initial concentrations were exposed to heat (60° C.).

The measurements of $R_1$ of water in the aggregated BSA solutions demonstrated virtually no dependence on the exposure time to heat and the concentration of the aggregates (FIG. 4(a)). Contrary to $R_1$, the transverse relaxation rate constant $R_2$ of water has grown markedly after heat exposure, and grows even more with the heat exposure time, and hence, with the increase in the concentration of BSA aggregates (see, FIG. 4(b)). As seen from FIG. 4(b), at higher initial concentrations of BSA (300-400 µM), the exposure to heat leads to significant, almost two-fold increase in the water relaxation rate constant $R_2$.

Figure 5A:
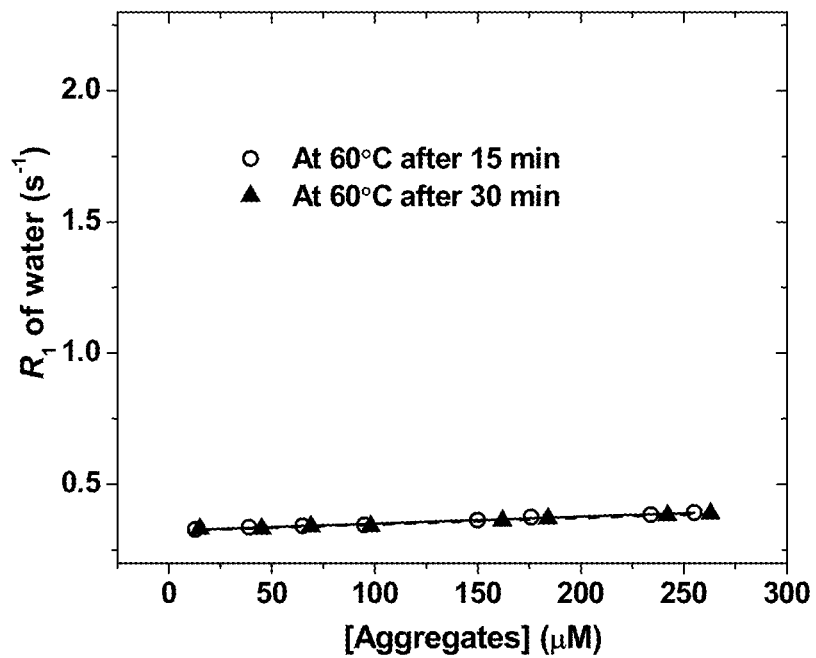
FIG. 5(a) illustrates the dependence of the longitudinal relaxation rate constant of water $R_1$ on the concentration of BSA aggregates at 60° C.
Figure 5B:
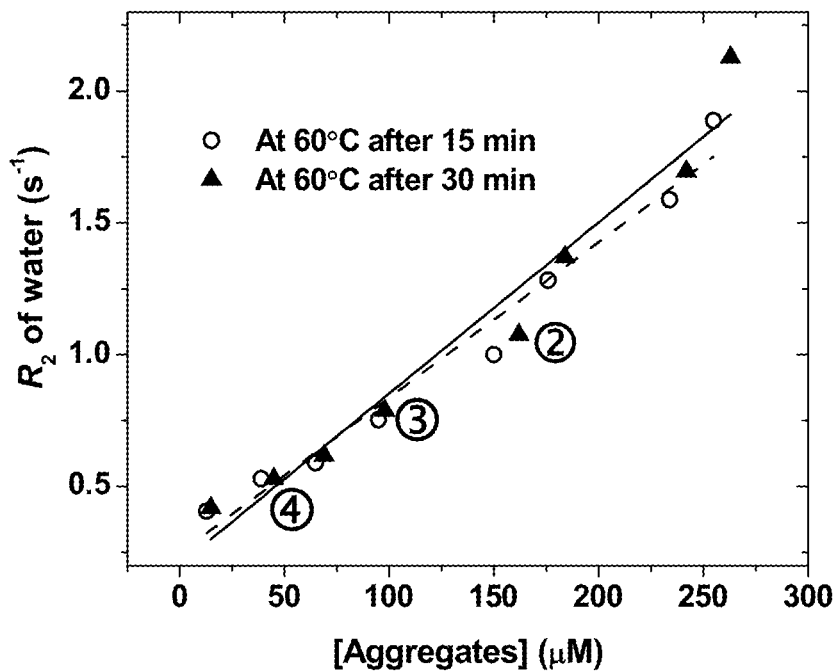
FIG. 5(b) illustrates the dependence of the transverse relaxation rate of water $R_2$ on the concentration of BSA aggregates at 60° C. The numbered labels correspond to vials 2, 3 and 4 shown in FIG. 2.

FIGS. 5(a) and 5(b) illustrate the relationship between $[C]_{agg}$ and water $R_1$ and $R_2$, respectively. It can be seen that $R_1$ is rather insensitive toward aggregation. In contrast, $R_2$ increases linearly with $[C]_{agg}$. Further, this linear dependency shows indifference to the duration of heating, suggesting that $R_2$ depends only on the extent of aggregation, not on how the aggregation was achieved.

The above results conclusively demonstrate the possibility of using the transverse relaxation rate constant $R_2$ of water to detect protein aggregation. As water is used as the solvent in all biopharmaceutical preparations, this technique can be used to quantify biopharmaceutical aggregation non-destructively. Such detections can be accomplished using NMR spectrometers, MM scanners, or bench-top MR relaxometers (e.g., BT-NMR/BT-MRI) [4]. The advantage of this approach is that it does not require opening the vial and hence is entirely non-destructive and non-disruptive. Because water is present in every biopharmaceutical preparations at very high concentration, this method is universally applicable to biopharmaceuticals and is amenable to full automation using bench-top relaxometers.

EXAMPLE 2

The initial concentration of all proteins in Example 2 for the study of heat-induced aggregation was 15 mg/mL which for BSA corresponds to 0.2 mM, and for γ-globulin corresponds to 0.1 mM. As in the Example 1, all solutions were prepared in PBS buffer at pH 7.4. Bovine serum albumin (BSA, lyophilized, 98% purity, molecular weight 66 kDa) and γ-globulin (from human blood, >99% purity, molecular weight 150 kDa) were purchased from Sigma Aldrich Inc., St. Louis, Mo., and were used without further purification. The temperatures used to induce aggregation were 55° C. (square, in FIGS. 6 and 7) and 60° C. (circle, in FIGS. 6 and 7) and exposure times at these temperatures varied from 2 minutes to 30 minutes (2, 5, 10, 15, 20, 25, and 30 minutes at each temperature). Different exposure times were used to attain different degrees of aggregation. The percentage of the aggregation was determined by SEC using the BioLogic DuoFlow® FPLC (Bio-Rad Laboratories, Hercules, Calif.) with UV-detector set at 280 nm. Column: Bio-Sil SEC (Bio-Rad Laboratories, Hercules, Calif.), 14 mL bed volume, particle size 5 μm, 5 kDa molecular weight cutoff. Injection sample volume: 100 μL. Eluent: PBS buffer at pH 7.4 with 1% sodium azide. Flow rate: 0.7 mL/min. Concentrations of the initial pure (non-aggregated) BSA and γ-globulin and their aggregates after the exposure to heat were estimated from the chromatographic peaks areas using the subroutine *Peak Fit Analysis* in Origin 8.1 (OriginLab Co., Northhampton, Mass.). Quality of the nonlinear peak fit was always $R^2=0.97$-$0.99$. The mean molecular weight of the aggregates was determined from dynamic light scattering (DLS) data based on the observed size distribution of the detected particles. The light-scattering experiments were carried out with light-scattering setup provided by Photocor Instruments (College Park, Md.) with He-Ne laser, photomultiplier and automatic goniometer. The sample in a cell was submerged into the silicon oil to ensure the uniform temperature of the measurements (25° C.) and to reduce possible stray light. Scattering profiles were detected at scattering angle θ=90°. The resulting auto-correlation function was processed using DynaLS software (SoftScientific, Tirat Carmel, Israel) to obtain size distributions of the aggregates and their mean molecular weights.

Figure 6A:
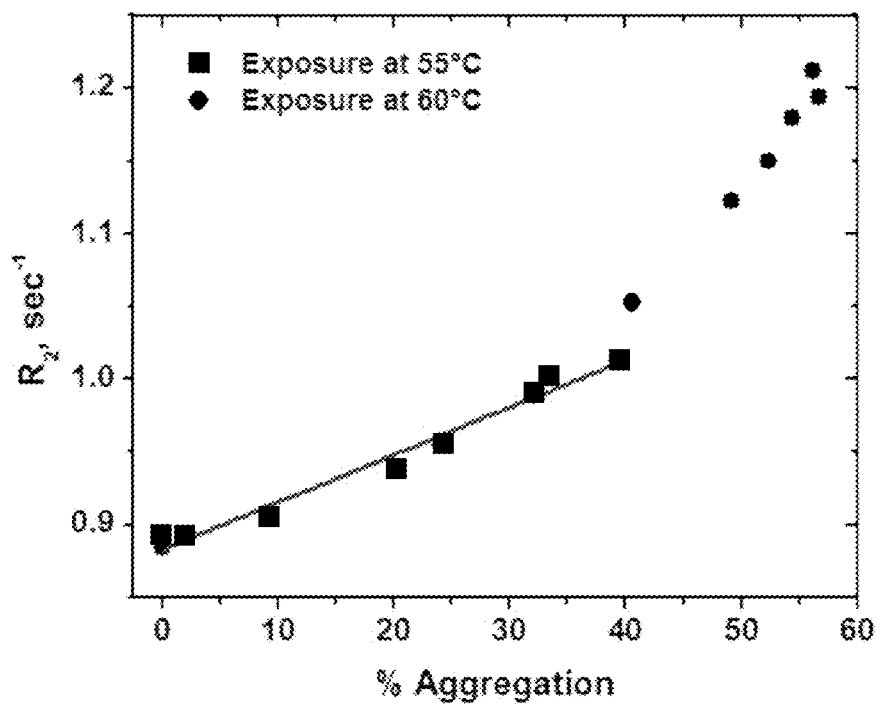
FIG. 6(a) illustrates the transverse relaxation rate of water $R_2$ relative to the percent aggregation of BSA.
Figure 6B:
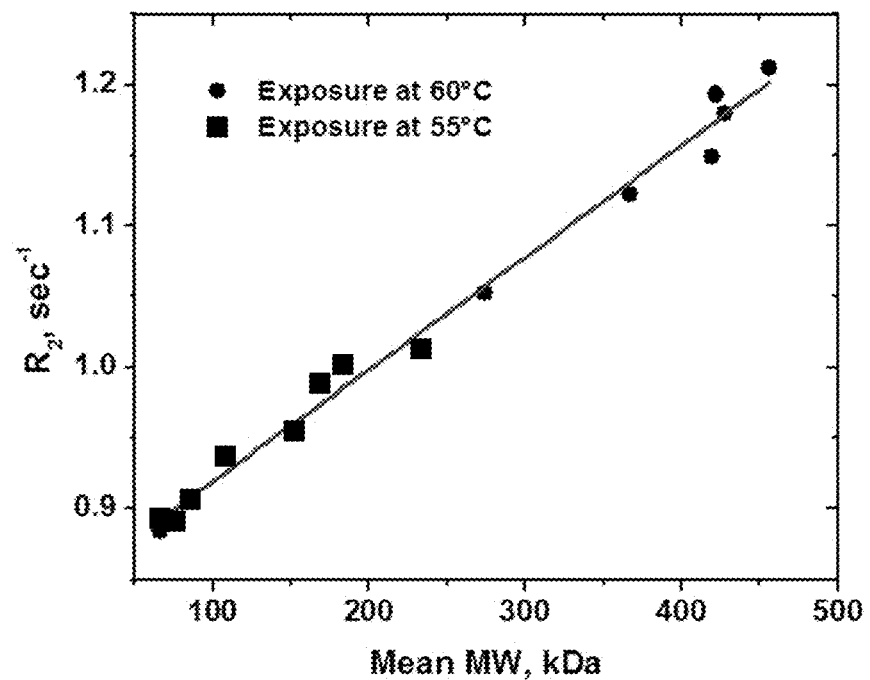
FIG. 6(b) illustrates the transverse relaxation rate of water $R_2$ relative to the mean molecular weight in kDa of BSA aggregates.
Figure 7A:
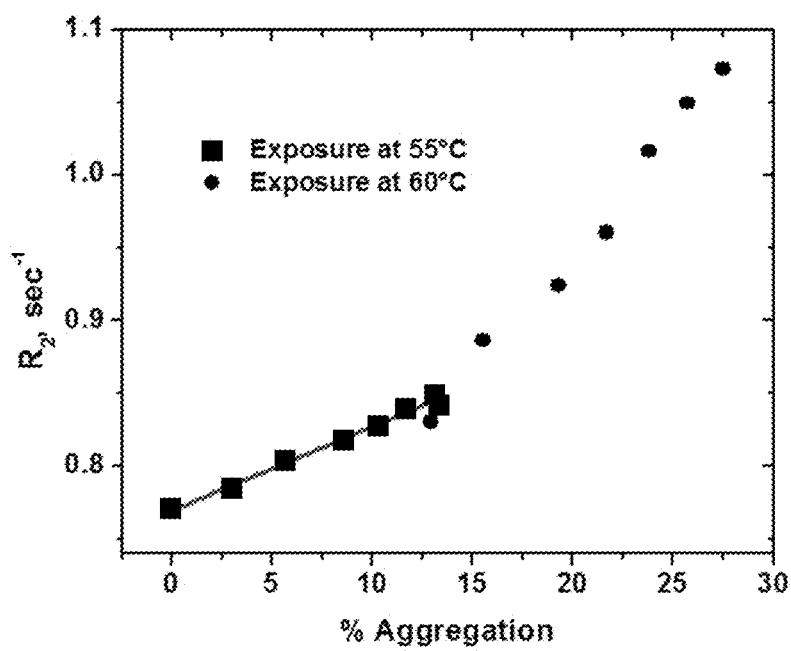
FIG. 7(a) illustrates the transverse relaxation rate of water $R_2$ relative to the percent aggregation of γ-globulin.
Figure 7B:
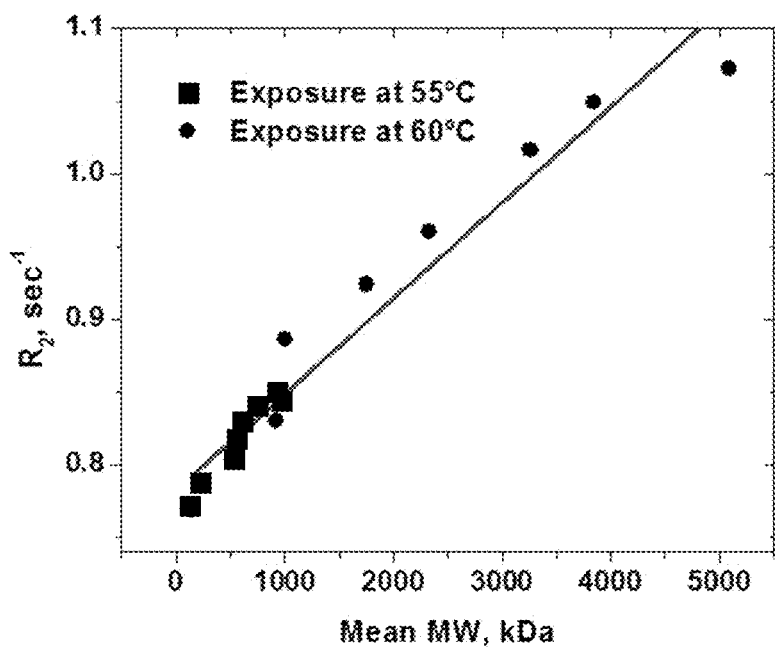
FIG. 7(b) illustrates the transverse relaxation rate of water $R_2$ relative to the mean molecular weight in kDa of γ-globulin aggregates.

The results for BSA are shown in FIGS. 6(*a*) and 6(*b*) and the results for γ-globulin are shown in FIGS. 7(*a*) and 7(*b*). The best-fit regression line based on the data at the respective temperatures with a high $R^2$ value (0.99) can be seen in all four figures, which verifies that if the user has a formula including the slope of the best-fit regression line or the figure itself and makes a non-destructive measurement of $R_2$ of water in the biopharmaceutical-containing product, they can determine the extent of aggregation and determine if the biopharmaceutical is overly degraded and unusable.

EXAMPLE 3

As introduced hereinabove, the present inventors surprisingly discovered that the transverse relaxation rate constant of water $R_2$ is very sensitive toward a variety of conditions of a complex mixture. For example, compositions comprising 10 mg/mL BSA with varying amounts of γ-globulin and hydroxypropylcellulose (HPC) were prepared, wherein the percentage of BSA (10 mg/mL) was held constant at 33% while the combined percentage of γ-globulin and HPC are held constant at 67%. As in the Examples 1 and 2, all solutions were prepared in PBS buffer at pH 7.4. Bovine serum albumin (BSA, lyophilized, 98% purity, molecular weight 66 kDa) and γ-globulin (from human blood, >99% purity, molecular weight 150 kDa) were purchased from Sigma Aldrich Inc., St. Louis, Mo., and were used without further purification. The measurement of the transverse relaxation rate of water $R_2$ was carried out as described hereinabove at 25° C.

Figure 8:
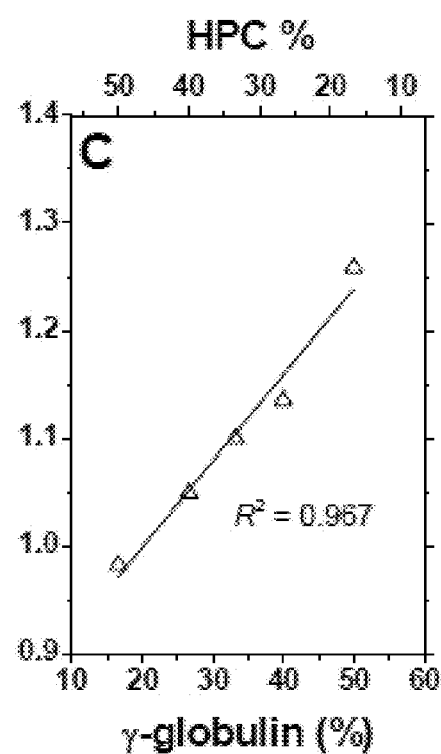
FIG. 8 illustrates the transverse relaxation rate of water $R_2$ relative to the variation of the percentage of HPC and γ-globulin in the composition.

The results are shown in FIG. 8, where it can be seen that the transverse relaxation rate of water $R_2$ varies with changes in the makeup of the complex mixture. Knowing this, changes in the makeup of all complex compositions should result in variations in the transverse relaxation rate of water $R_2$ and hence permit the identification of counterfeit compositions.

EXAMPLE 4

The present inventors also determined that the transverse relaxation rate of water $R_2$ is sensitive to the chemical modifications of peptides. For example, both N-terminal acetylation and C-terminal amidation induced readily detectable change in water $R_2$ (see, e.g., Table 2). Note that N-terminal acetylation, which blocks a positive charge, was implemented in a peptide with 6 positively changed amino acids while C-terminal amidation, which blocks a negative charge, was implemented in a peptide with 6 negatively charged amino acids. Hence, each modification turned off 1 out of 7 charges. The fact that the transverse relaxation rate of water $R_2$ varied, attests to the sensitivity of this method.

TABLE 2

Impact of peptide N-, C-terminal blockage on water $R_2$ (8 mM peptide, pH 7.4)

| N-terminal acetylation | charge | water $R_2$ (s$^{-1}$) | C-terminal amidation | charge | water $R_2$ (s$^{-1}$) |
|---|---|---|---|---|---|
| H$_2$N—KW(KA)$_3$KWK-amide | +7 | 1.15 | acetyl-EW(EA)$_3$EWE-OH | −7 | 0.53 |
| acetyl-KW(KA)$_3$KWK-amide | +6 | 1.33 | acetyl-EW(EA)$_3$EWE-amide | −6 | 0.60 |

Charge refers to the total number of chargeable groups in a peptide (side chains + terminals)

The results are shown in Table 2, where it can be seen that the transverse relaxation rate of water $R_2$ varies with chemical modifications Knowing this, minor modifications to compounds in compositions should result in variations in the transverse relaxation rate of water $R_2$ and hence permit the identification of counterfeit compositions.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

1. Krayukhina, E.; Uchiyama, S.; Nojima, K.; Okada, Y.; Hamaguchi, I.; Fukui, K., *J. Biosci. Bioeng.* 2012, 115, 104-110.
2. Oliva, A.; Fariña, J. B.; Llabrés, M., *Int. J. Pharm.* 1996, 143, 163-170.
3. Dalvit, C.; Flocco, M.; Knapp, S.; Mostardini, M.; Perego, R.; Stockman, B. J.; Veronesi, M.; Varasi, M., *J. Am. Chem. Soc.* 2002, 124, 7702-7709.
4. Metz, H.; Mäder, K., *Int. J. Pharm.* 2008, 364, 170-178.
5. Bloembergen, N.; Purcell, E. M., Pound, R. V., *Phys. Rev.* 1948, 73, 679-746.
6. Fanali, G.; di Massi, A.; Trezza, V.; Marino, M.; Fasano, M.; Ascenzi, P., *Mol. Asp. Med.* 2012, 33, 209-290.

7. Saso, L.; Valentini, G.; Grippa, E.; Leone, M. G.; Silvestrini, B., *Res. Commun. Pathol. Pharmacol.* 1998, 102, 15-28.
8. Mao, X.; Ye, C., *Concepts Magn. Reson.* 1997, 9, 173.

What is claimed is:

1. A method of assessing the quality of a post-production product comprising a biopharmaceutical, said method comprising:
    measuring a transverse relaxation rate of water $R_2$ of the post-production product at a specified temperature; and
    comparing the measured $R_2$ of water of the post-production product to a maximum $R_2$ of water of the product at the specified temperature at the time of production, wherein if the measured $R_2$ of water of the post-production product is greater than the maximum $R_2$ of water for the product at the time of production, the product should not be distributed or used.

2. The method of claim 1, wherein the product is contained in a vial.

3. The method of claim 2, wherein the transverse relaxation rate of water $R_2$ is measured without opening the vial or otherwise accessing the contents of the vial containing the product.

4. The method of claim 2, wherein the transverse relaxation rate of water $R_2$ can be measured without adding any additives to the vial containing the product.

5. The method of claim 1, wherein the biopharmaceutical is selected from the group consisting of a protein, a peptide, a nucleic acid, and a polysaccharide.

6. The method of claim 1, wherein the biopharmaceutical is selected from the group consisting of a hormone, a blood factor, an interferon, a haematopoietic growth factor, an interleukin-based product, a vaccine, and a monoclonal antibody.

7. The method of claim 1, wherein the biopharmaceutical is selected from the group consisting of bovine serum albumin, human serum albumin, human γ-globulin, insulin, glucagon, gonadotrophins, growth hormone, erythropoetin, Factor VIII, Factor IX, thrombolytic agents, interferon-α, interferon-β, interferon-γ, interleukin-2, influenza vaccine, adalimumab, rituximab, infliximab, trastuzumab, ustekinumab, denosumab, golimumab, Fc fragments, Fab fragments, intravenous immunoglobulin (IVIG), tumor necrosis factor, abatacept, alefacept, etanercept, denileukin diftitox, OPTISON, NEUPOGEN, albumin, and ribonuclease A.

8. The method of claim 1, wherein the $R_2$ is measured using nuclear magnetic resonance (NMR) or magnetic resonance imaging (MRI).

9. The method of claim 1, wherein the control composition comprises at least one compound having a known concentration and sample composition is represented as comprising the same compound(s) having the same concentration(s).

* * * * *